(12) United States Patent
Ushiroda

(10) Patent No.: US 11,582,427 B2
(45) Date of Patent: Feb. 14, 2023

(54) MEDICAL IMAGE PROCESSING APPARATUS AND MEDICAL OBSERVATION SYSTEM

(71) Applicant: Sony Olympus Medical Solutions Inc., Tokyo (JP)

(72) Inventor: Hiroshi Ushiroda, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 8 days.

(21) Appl. No.: 17/134,521

(22) Filed: Dec. 28, 2020

(65) Prior Publication Data
US 2021/0244261 A1 Aug. 12, 2021

(30) Foreign Application Priority Data
Feb. 10, 2020 (JP) .............................. JP2020-020775

(51) Int. Cl.
*G06T 1/00* (2006.01)
*H04N 7/18* (2006.01)
(Continued)

(52) U.S. Cl.
CPC ........... *H04N 7/183* (2013.01); *A61B 1/0005* (2013.01); *A61B 1/000094* (2022.02); *A61B 1/043* (2013.01); *A61B 1/0638* (2013.01); *A61B 1/0655* (2022.02); *H04N 5/2256* (2013.01); *H04N 5/23229* (2013.01); *H04N 5/272* (2013.01); *H04N 7/18* (2013.01);
(Continued)

(58) Field of Classification Search
CPC ... A61B 1/00009; A61B 1/0005; A61B 1/043; A61B 1/0638; A61B 1/00078; A61B 1/00105; A61B 1/00114; A61B 1/00117; A61B 1/042; A61B 1/063; A61B 1/0646; A61B 1/0669; A61B 1/0684; A61B 1/000094; A61B 1/00186; H04N 5/2256; H04N 5/23229; H04N 5/272; H04N 7/18; H04N 2005/2255; G06K 9/6201; G06T 1/00
See application file for complete search history.

(56) References Cited

U.S. PATENT DOCUMENTS 6,293,911 B1 * 9/2001 Imaizumi ........... A61B 1/00009
600/178
6,527,708 B1 * 3/2003 Nakamura ........... A61B 1/0005
600/109

(Continued)

FOREIGN PATENT DOCUMENTS

JP 6110887 B2 4/2017

*Primary Examiner* — Frank F Huang
(74) *Attorney, Agent, or Firm* — Xsensus LLP

(57) ABSTRACT

A medical image processing apparatus includes an image processor configured to: receive a plurality of first image data captured at different times and generated by illumination of light in a first wavelength band in sequence; receive a plurality of second image data captured at different times and generated by illumination of light in a second wavelength band different from the first wavelength band in sequence; generate first and second images based on the received first and second image data, respectively; and output the generated first image and second image to a display in chronological order of the first and second images and in accordance with a preset display pattern of the first and second images.

14 Claims, 12 Drawing Sheets

(51) Int. Cl.

| | | |
|---|---|---|
| *H04N 5/232* | (2006.01) | |
| *H04N 5/225* | (2006.01) | |
| *H04N 5/272* | (2006.01) | |
| *A61B 1/00* | (2006.01) | |
| *A61B 1/04* | (2006.01) | |
| *A61B 1/06* | (2006.01) | |
| *G06K 9/62* | (2022.01) | |

(52) U.S. Cl.
CPC ....... *A61B 1/00078* (2013.01); *A61B 1/00105* (2013.01); *A61B 1/00114* (2013.01); *A61B 1/00117* (2013.01); *A61B 1/042* (2013.01); *A61B 1/063* (2013.01); *A61B 1/0646* (2013.01); *A61B 1/0669* (2013.01); *A61B 1/0684* (2013.01); *G06K 9/6201* (2013.01); *G06T 1/00* (2013.01); *H04N 2005/2255* (2013.01)

(56) References Cited

U.S. PATENT DOCUMENTS

| | | | |
|---|---|---|---|
| 10,231,626 B2* | 3/2019 | Steinbach | A61B 5/0071 |
| 10,602,918 B2* | 3/2020 | King | A61B 1/0638 |
| 10,646,110 B2* | 5/2020 | Fukuda | A61B 1/05 |
| 2003/0231791 A1* | 12/2003 | Torre-Bueno | G06T 5/50 |
| | | | 382/133 |
| 2004/0245350 A1* | 12/2004 | Zeng | A61B 1/042 |
| | | | 236/77 |
| 2006/0256191 A1* | 11/2006 | Iketani | A61B 1/0005 |
| | | | 348/65 |
| 2012/0183198 A1* | 7/2012 | Zahniser | G06T 7/0014 |
| | | | 382/133 |

* cited by examiner

MEDICAL IMAGE PROCESSING APPARATUS AND MEDICAL OBSERVATION SYSTEM

CROSS-REFERENCE TO RELATED APPLICATION

This application claims priority from Japanese Application No. 2020-020775, filed on Feb. 10, 2020, the contents of which are incorporated by reference herein in its entirety.

BACKGROUND

The present disclosure relates to a medical image processing apparatus and a medical observation system.

There are known techniques by which, in a medical or industrial camera, a fluorescence image that illustrates a specific portion acquired by capturing an optical image in an excitation light band by a first imaging unit and a visible light image acquired by capturing an optical image of a visible light region by a second imaging unit are added to each pixel at a predetermined ratio to thereby generate a superimposed image in which the fluorescence image is superimposed on the visible light image (see, for example, see Japanese Patent No. 6110887).

SUMMARY

Japanese Patent No. 6110887 has a problem of complicated processing because the separately processed fluorescence image is superimposed on the visible light image.

There is a need for a medical observation system and a medical image processing apparatus capable of perceiving a visible light image and a fluorescence image by simple processing.

According to one aspect of the present disclosure, there is provided a medical image processing apparatus including an image processor configured to: receive a plurality of first image data captured at different times and generated by illumination of light in a first wavelength band in sequence; receive a plurality of second image data captured at different times and generated by illumination of light in a second wavelength band different from the first wavelength band in sequence; generate first and second images based on the received first and second image data, respectively; and output the generated first image and second image to a display in chronological order of the first and second images and in accordance with a preset display pattern of the first and second images.

DETAILED DESCRIPTION

Figure 1:
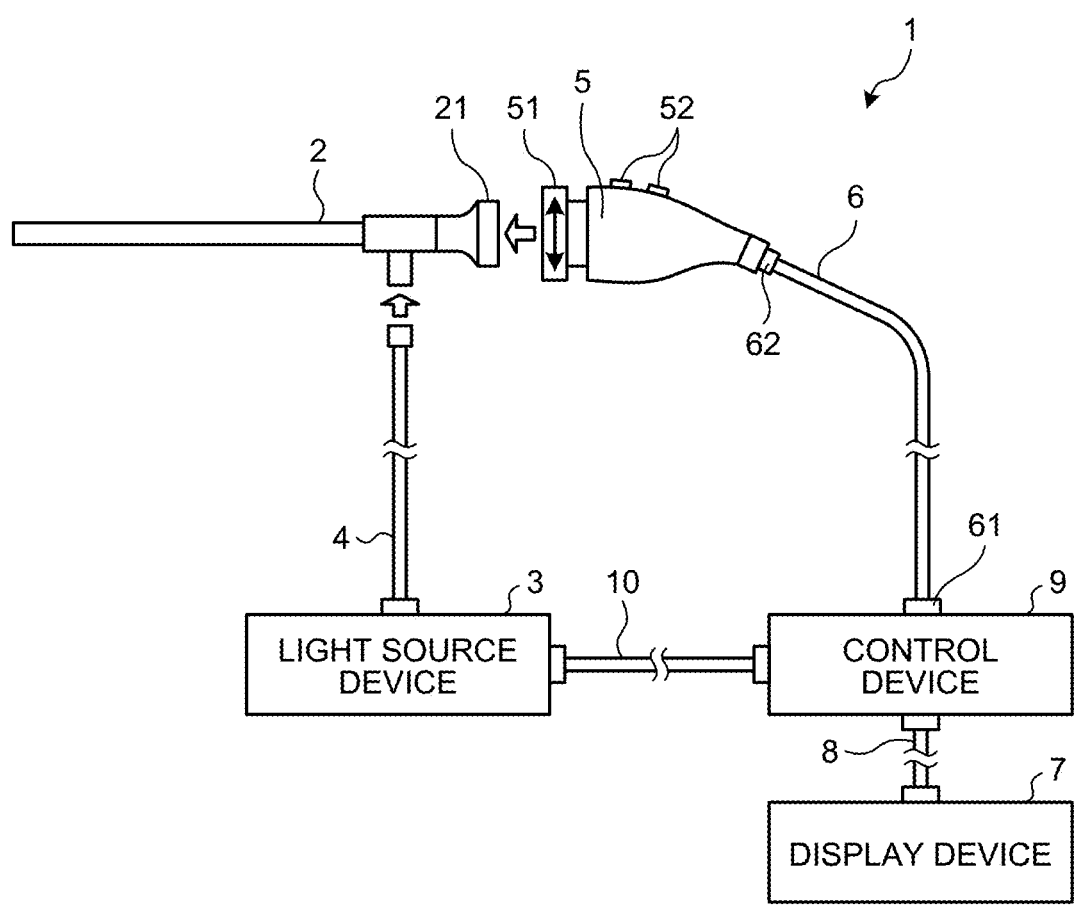
FIG. 1 is a diagram illustrating a schematic configuration of an endoscope system according to a first embodiment.

Hereinafter, modes for carrying out the present disclosure (hereinafter, referred to as "embodiments") will be described. In relation to the embodiments, as an example of a system including a medical image processing apparatus according to the present disclosure, a medical endoscope system that captures and displays an image of a subject such as a patient will be described. The present disclosure is not limited to the embodiments. In description of the drawings, the same portions are denoted by the same reference numerals.

First Embodiment

FIG. 1 is a diagram illustrating a schematic configuration of an endoscope system according to a first embodiment. An endoscope system 1 illustrated in FIG. 1 is a system that is used in the medical field to observe a subject such as a human or animal living body by inserting it into the living body of the subject and display a captured image of the inside of the subject. In the first embodiment, as the endoscope system 1, a rigid endoscope system using a rigid mirror (insertion portion 2) illustrated in FIG. 1 will be described. However, the present disclosure is not limited to this but, for example, may be a flexible endoscope system.

The endoscope system 1 illustrated in FIG. 1 includes the insertion portion 2, a light source device 3, a light guide 4, a camera head 5 (endoscope imaging device), a first transmission cable 6, a display device 7, a second transmission cable 8, a control device 9, and a third transmission cable 10.

The insertion portion 2 is hard or at least partially flexible and has an elongated shape. The insertion portion 2 is to be inserted into a subject such as a patient. The insertion portion 2 is internally configured with one or a plurality of lenses, and is provided with an optical system for coupling observation images.

One end of the light guide 4 is connected to the light source device 3. Under the control of the control device 9, the light source device 3 emits (supplies) white light for illuminating the inside of the subject to one end of the light guide 4, and emits (supplies) excitation light or infrared light to drug administered or sprayed to the subject. The light source device 3 is configured with semiconductor laser elements such as a light emitting diode (LED) light source or a laser diode (LD). The light source device 3 and the control device 9 may be configured to communicate individually as illustrated in FIG. 1 or may be integrated.

One end of the light guide 4 is detachably connected to the light source device 3, and the other end is detachably connected to the insertion portion 2. The light guide 4 guides the light emitted from the light source device 3 from one end to the other end and supplies the light to the insertion portion 2.

An eyepiece 21 of the insertion portion 2 is detachably connected to the camera head 5. Under the control of the control device 9, the camera head 5 generates image data (imaging signal) by capturing an observation image formed by the insertion portion 2, and outputs this image data. The camera head 5 includes an operation ring portion 51 rotatably provided in the circumferential direction, and a plurality of input units 52 that receive inputs of instruction signals for instructing various operations of the endoscope system 1.

One end of the first transmission cable 6 is detachably connected to the control device 9 via a first connector unit 61, and the other end is connected to the camera head 5 via a second connector unit 62. The first transmission cable 6 transmits the image data output from the camera head 5 to the control device 9, and transmits control signals, synchronization signals, clock signals, power, etc. output from the control device 9 to the camera head 5.

The display device 7 is connectable to the control device 9 via the second transmission cable 8 and displays a display image based on the image data processed by the control device 9 under the control of the control device 9.

One end of the second transmission cable 8 is detachably connected to the display device 7, and the other end is detachably connected to the control device 9. The second transmission cable 8 transmits a display image based on the image data processed by the control device 9 to the display device 7.

The control device 9 is configured with a memory and a processor having hardware such as a central processing unit (CPU), a graphics processing unit (GPU), an application specific integrated circuit (ASIC), and a field programmable gate array (FPGA). The control device 9 comprehensively controls the operations of the light source device 3, the camera head 5, and the display device 7 via the first transmission cable 6, the second transmission cable 8, and the third transmission cable 10, according to programs recorded in the memory. The control device 9 also performs various kinds of image processing on the image data input from the camera head 5 via the first transmission cable 6 and outputs the image data to the second transmission cable 8.

One end of the third transmission cable 10 is detachably connected to the light source device 3, and the other end is detachably connected to the control device 9. The third transmission cable 10 transmits the control signal from the control device 9 to the light source device 3.

Figure 2:
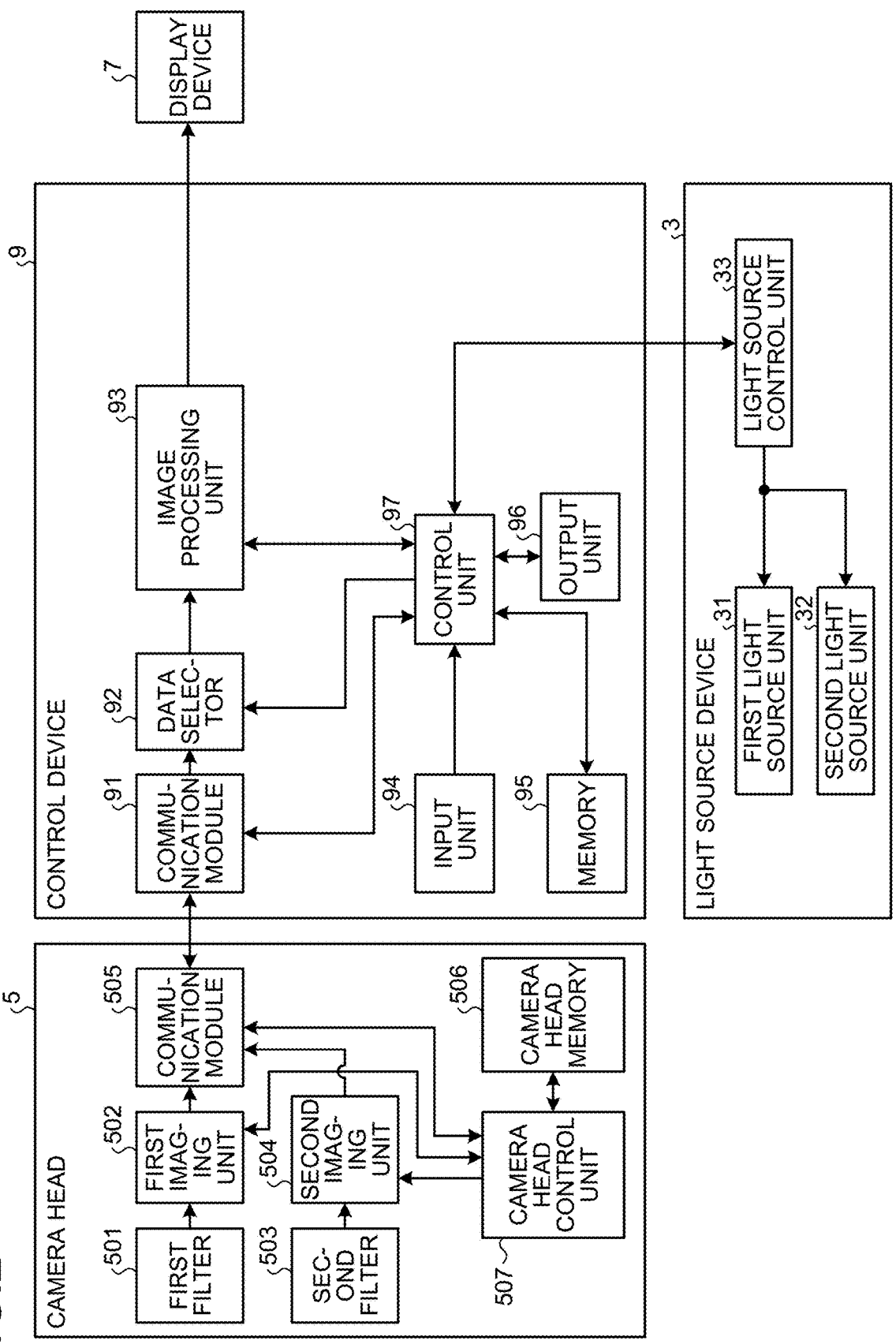
FIG. 2 is a block diagram illustrating a configuration of a camera head, a control device, and a light source device illustrated in FIG. 1.

Next, functional configurations of the light source device 3, the camera head 5, and the control device 9 will be described. FIG. 2 is a block diagram illustrating the functional configurations of the light source device 3, the camera head 5, and the control device 9 included in the endoscope system 1. For convenience of explanation, FIG. 2 does not illustrate the insertion portion 2, the light guide 4, the first transmission cable 6, the second transmission cable 8, and the third transmission cable 10.

First, the configuration of the light source device 3 will be described.

The light source device 3 includes a first light source unit 31, a second light source unit 32, and a light source control unit 33.

Under the control of the light source control unit 33, the first light source unit 31 emits a pulse of white light, thereby supplying the insertion portion 2 with the white light to be irradiated to the subject. The first light source unit 31 is configured with a red semiconductor laser element capable of emitting red (wavelength band of 600 nm to 700 nm) light, a green semiconductor laser element capable of emitting green (wavelength band of 500 nm to 600 nm) light, and a blue semiconductor laser element capable of emitting blue (wavelength band of 400 nm to 500 nm) light. The first light source unit 31 is configured with red, green, and blue semiconductor laser elements, but the present disclosure is not limited to this, and the first light source unit 31 may use a white semiconductor laser element capable of emitting white light. The first light source unit 31 does not need to be a semiconductor laser element but may be, for example, a LED or the like. The first light source unit 31 is not limited to a simultaneous lighting type that emits simultaneously red, green, and blue light, but may be a surface sequential lighting type that sequentially emits red, green, and blue light. The wavelength bands described above are examples, and the wavelength ranges may be appropriately changed.

Under the control of the light source control unit 33, the second light source unit 32 emits a pulse of infrared light to be emitted to the subject via the insertion portion 2. Specifically, under the control of the light source control unit 33, the second light source unit 32 emits infrared light (wavelength band of 700 to 1000 nm) that excites a drug (fluorescent substance) injected into the subject, thereby to supply the infrared light to the insertion portion 2. The second light source unit 32 is configured with a semiconductor laser element capable of emitting light (700 to 1000 nm) that excites a fluorescent substance, a filter that transmits only light of a predetermined wavelength band, and the like. In the following, the light emitted by the second light source unit 32 will be described as infrared light. However, the present disclosure is not limited to this. For example, the second light source unit 32 may emit light (wavelength band of 405 nm or so) to be used for photo dynamic diagnosis (PDD) observation by which a light-sensitive substance such as a hematoporphyrin derivative is accumulated in the tumor tissue in advance and then fluorescent light is observed, light (wavelength band of 390 to 470 nm+wavelength band of 540 to 560 nm) to be used for auto fluorescence imaging (AFI) observation by which self-emitted light from a fluorescent substance such as collagen is observed, or the like.

The light source control unit 33 controls the light emission of the first light source unit 31 and the second light source unit 32 under the control of the control device 9. The light source control unit 33 is configured with a memory and a processor having hardware such as a CPU, ASIC, and FPGA.

Next, the configuration of the camera head 5 will be described.

The camera head 5 includes a first filter 501, a first imaging unit 502, a second filter 503, a second imaging unit 504, a communication module 505, a camera head memory 506, and a camera head control unit 507. In addition to these, the camera head 5 includes a lens unit that performs auto focus (AF) to change the focal position and optical zoom to change the focal length by a drive unit (not illustrated)

moving a lens along an optical axis direction under the control of the camera head control unit 507.

The first filter 501 transmits light in a wavelength band emitted by the first light source unit 31, and blocks (reflects) light in wavelength bands other than this wavelength band.

The second filter 503 transmits light in a wavelength band emitted by the second light source unit 32 and light in a wavelength band of fluorescence emitted by an excited fluorescent substance, and blocks (reflects) light in wavelength bands other than these wavelength bands. At this time, the wavelength band of the light emitted by the second light source unit 32 and the wavelength band of fluorescence emitted by the excited fluorescent substance may overlap.

The filters may block a portion of the light in the wavelength band to be transmitted. The filters may transmit a portion of the light in the wavelength band to be blocked.

The first imaging unit 502 and the second imaging unit 504 are configured with an imaging element that receives light (subject image) having passed through the filters, performs photoelectric conversion to generate image data (RAW data), and outputs the image data to the communication module 505, under the control of the camera head control unit 507. The first imaging unit 502 and the second imaging unit 504 are configured with a charge coupled device (CCD), a complementary metal oxide semiconductor (CMOS), or the like.

In a normal observation mode in which the first light source unit 31 irradiates the subject with white light, the first imaging unit 502 captures the light having passed through the first filter 501 to generate first image data and outputs a first image based on the first image data (hereinafter, simply referred to as "first image") to the communication module 505.

In a special observation mode in which the second light source unit 32 captures an image by irradiating a drug administered to the subject with infrared light, the second imaging unit 504 captures the light having passed through the second filter 503 to generate second image data and outputs a second image based on the second image data (hereinafter, simply referred to as "second image") to the communication module 505.

The communication module 505 outputs various signals transmitted from the control device 9 via the first transmission cable 6 to individual units in the camera head 5. The communication module 505 also performs parallel-serial conversion processing or the like on the first image and the second image generated by the imaging units, information relating to the current state of the camera head 5, and the like and outputs the same to the control device 9 via the first transmission cable 6.

The camera head memory 506 stores camera head information for identifying the camera head 5 and various programs to be executed by the camera head 5. The camera head information includes the numbers of pixels of the imaging units, the pixel pitch, the identification ID of the camera head 5, and the like. The camera head memory 506 is configured with a volatile memory, a non-volatile memory, and the like.

The camera head control unit 507 controls the operations of individual units constituting the camera head 5 based on various signals input from the communication module 505. The camera head control unit 507 may change imaging conditions (shutter speed, etc.) between the capturing of the first image and the capturing of the second image. The camera head control unit 507 is configured with a memory and a processor having hardware such as a CPU.

Next, the configuration of the control device 9 will be described.

The control device 9 includes a communication module 91, a data selector 92, an image processing unit 93, an input unit 94, a memory 95, an output unit 96, and a control unit 97.

The communication module 91 outputs various signals including the imaging signal input from the camera head 5 to the control unit 97 and the data selector 92. The communication module 91 also transmits various signals input from the control unit 97 to the camera head 5. Specifically, the communication module 91 performs parallel-serial conversion processing or the like on the signals input from the control unit 97 and outputs the signals to the camera head 5. The communication module 91 further performs serial-parallel conversion processing or the like on the signals input from the camera head 5 and outputs the signals to individual units constituting the control device 9.

The data selector 92 selects either the first image or the second image input from the camera head 5 via the communication module 91 under the control of the control unit 97, and outputs the selected image (image data) to the image processing unit 93.

The image processing unit 93 performs signal processing such as noise reduction processing and A/D conversion processing on the first image or the second image selected by the data selector 92. The image processing unit 93 also performs various kinds of image processing on the input first image or second image under the control of the control unit 97 and outputs the image to the display device 7. The predetermined image processing includes various kinds of publicly known image processing such as interpolation processing, color correction processing, color enhancement processing, and contour enhancement processing. The image processing unit 93 may change processing conditions (gain, hue, chroma, etc.) between the first image and the second image. The image processing unit 93 is configured with a memory and a processor having hardware such as a GPU, FPGA, or CPU.

Moreover, in the present disclosure, the first image and the second image may be alternatively displayed; however, the second image may be superimposed on the first image when recording a still image, for example, in purpose of recording a medical treatment or the like. Therefore, the image processing unit 93 may obtain and compose the first image captured by the first imaging unit 502 and the second image captured by the second imaging unit 504, and the composed image may be stored in the below-described memory 95.

The input unit 94 is configured with a keyboard, a mouse, a touch panel, or the like. The input unit 94 accepts inputs of various kinds of information by the user's operation.

The memory 95 is configured with a volatile memory, a non-volatile memory, a frame memory, and the like. The memory 95 stores various programs to be executed by the endoscope system 1 and various kinds of data to be used during processing. The memory 95 may also store the first image and the second image in association with the display timings (frame numbers). The memory 95 may further include a memory card or the like that may be attached to the control device 9.

The output unit 96 is configured with a speaker, a printer, a display, and the like. The output unit 96 outputs various kinds of information about the endoscope system 1.

The control unit 97 comprehensively controls individual units constituting the endoscope system 1. The control unit 97 sets an observation mode (normal observation mode or special observation mode) based on the instruction input into the input unit 94, and stores information about the set mode in the memory 95. The control unit 97 is configured with hardware such as a memory and a CPU.

Figure 3:
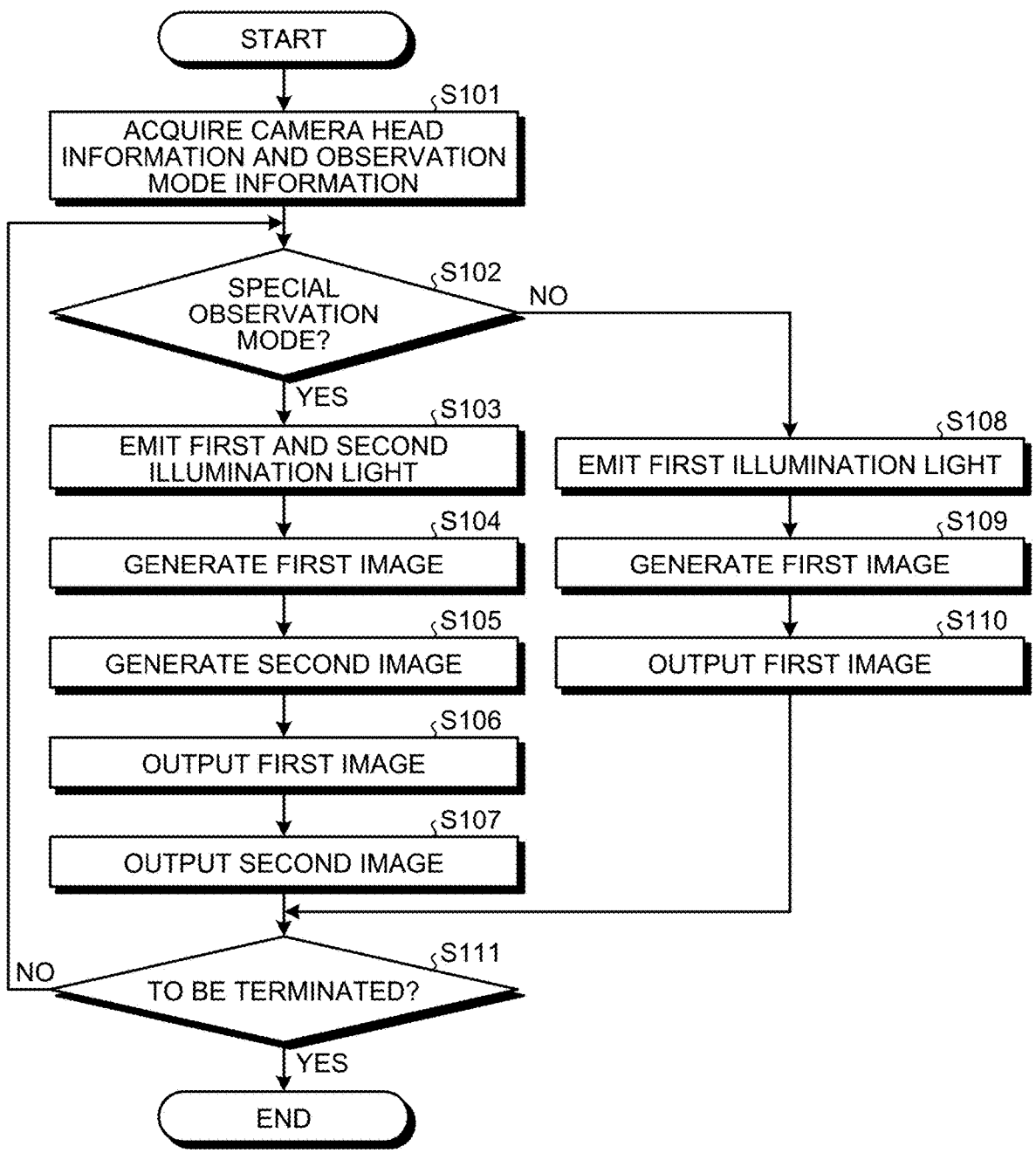
FIG. 3 is a flowchart illustrating an outline of processing executed by the endoscope system according to the first embodiment.

Next, the processing executed by the endoscope system 1 will be described. FIG. 3 is a flowchart illustrating an outline of the processing executed by the endoscope system 1.

First, the control unit 97 acquires camera head information from the camera head 5 via the communication module 91 and acquires observation mode information indicating the current observation mode of the endoscope system 1 from the memory 95 (step S101).

Subsequently, the control unit 97 determines whether the endoscope system 1 is in the special observation mode, based on the observation mode information acquired from the memory 95 (step S102). When the control unit 97 determines that the endoscope system 1 is in the special observation mode (step S102: Yes), the endoscope system 1 proceeds to step S103, which will be described later. On the other hand, when the control unit 97 determines that the endoscope system 1 is not in the special observation mode (step S102: No), the endoscope system 1 proceeds to step S108, which will be described later.

In step S103, the control unit 97 causes the light source device 3 to emit white light and infrared light. In this case, in the light source device 3, the first light source unit 31 emits white light, and the second light source unit 32 emits infrared light.

In step S104, among the light emitted from the subject, the first imaging unit 502 receives a component of the white light that has passed through the first filter 501, and performs photoelectric conversion on the light to generate an image signal. This image signal is a signal including the first image data. At this time, the data selector 92 selects the image signal input from the first imaging unit 502 and outputs it to the image processing unit 93.

Figure 4:
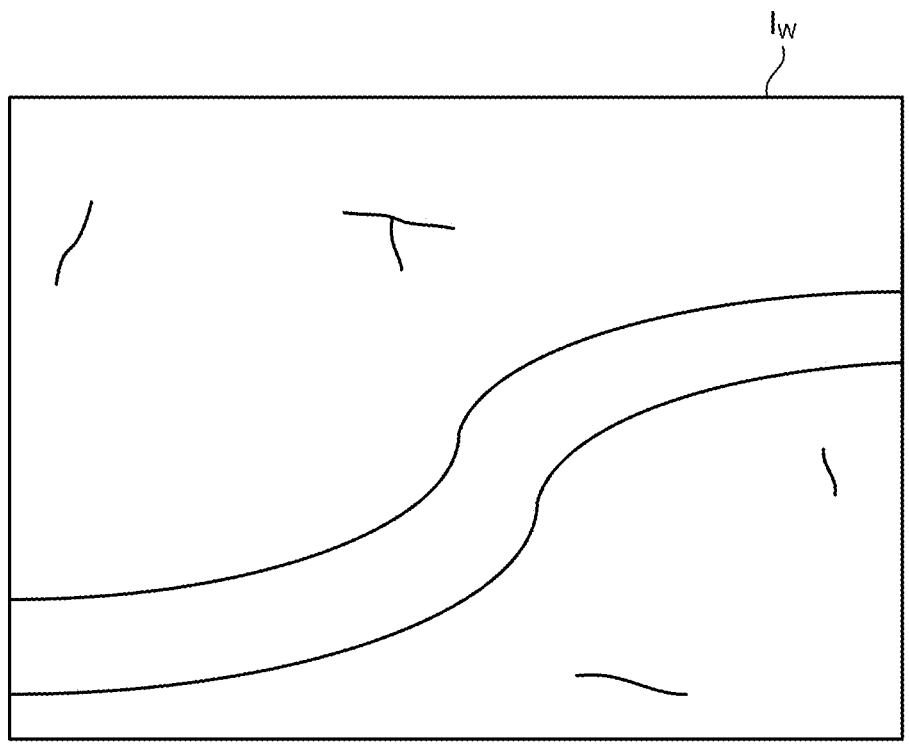
FIG. 4 is a diagram schematically illustrating an example of a first image observed by light from a first light source unit.

Under the control of the control unit 97, the image processing unit 93 acquires an image signal from the first imaging unit 502 via the communication module 505, the communication module 91, and the data selector 92. FIG. 4 is a diagram schematically illustrating an example of a first image observed by the light from the first light source unit. For example, the image processing unit 93 acquires a first image $I_W$ as illustrated in FIG. 4.

Also, in step S105, among the light emitted from the subject, the second imaging unit 504 receives a component of the infrared light that has passed through the second filter 503, and performs photoelectric conversion on the light to generate an image signal. This image signal is a signal including the second image data. At this time, the data selector 92 selects the image signal input from the second imaging unit 504 and outputs it to the image processing unit 93.

Figure 5:
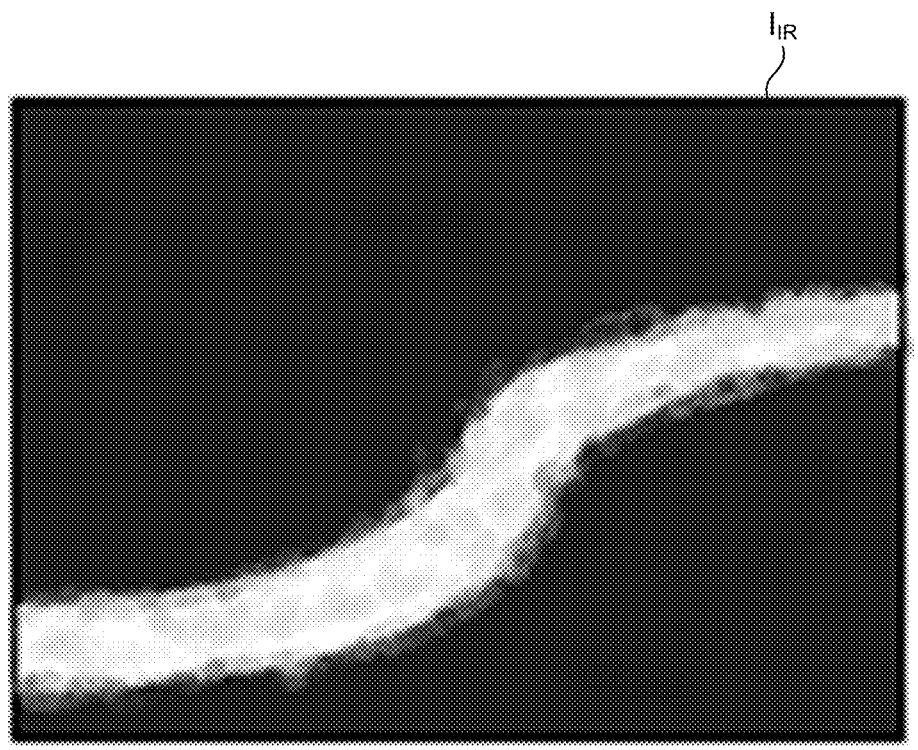
FIG. 5 is a diagram schematically illustrating an example of a second image observed by light from a second light source unit.

Under the control of the control unit 97, the image processing unit 93 acquires an image signal from the second imaging unit 504 via the communication module 505, the communication module 91, and the data selector 92. FIG. 5 is a diagram schematically illustrating an example of a second image observed by the light from the second light source unit. For example, the image processing unit 93 acquires a second image $I_{IR}$ as illustrated in FIG. 5. In the present embodiment, the second image is an image obtained by capturing a fluorescence image excited by infrared light.

The image signal generated by the first imaging unit 502 and the image signal generated by the second imaging unit 504 are alternately input to the image processing unit 93 in accordance with the signal selection of the data selector 92.

The image signal input by the first imaging unit 502 at this time includes image data (first image data) captured at different times, and the image signal input by the second imaging unit 504 includes image data (second image data) captured at different times. These image data (first and second image data) are input to the image processing unit 93 in order according to a preset display pattern in chronological order. In the first embodiment, the image processing unit 93 outputs images to the display device 7 according to a display pattern in which images based on white light (first image) and images based on infrared light (second image) are alternately displayed.

The image processing unit 93 outputs the first image to the display device 7 (step S106). After that, the image processing unit 93 outputs the second image to the display device 7 (step S107). The image processing unit 93 alternately outputs the first image and the second image at different times, so that the first image and the second image are sequentially displayed at different times on the display device 7.

Figure 6:
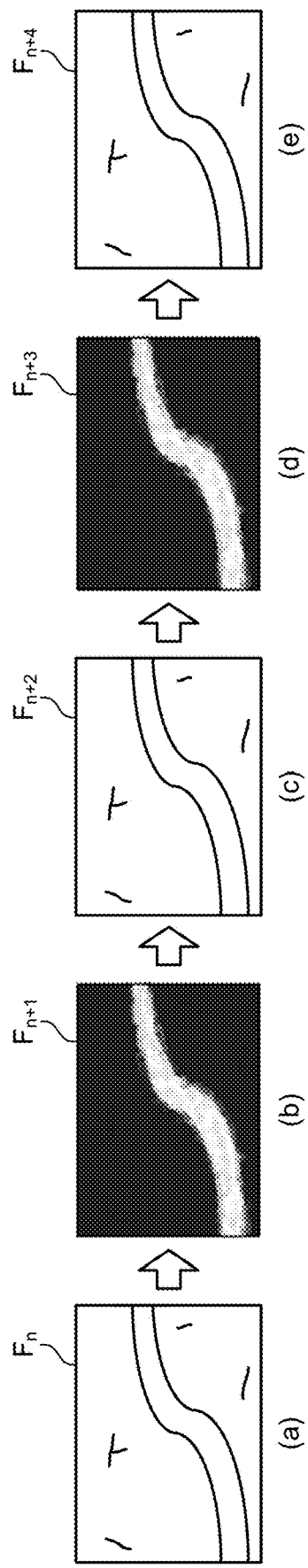
FIG. 6 is a diagram illustrating an example of display order of first and second images.

FIG. 6 is a diagram illustrating an example of display order of first and second images. The image processing unit 93 outputs the first image (for example, the first image $I_W$ illustrated in FIG. 4) with the frame numbers $F_n$, $F_{n+2}$, $F_{n+4}$, . . . to be displayed on the display device 7, and outputs the second image (for example, the second image $I_{IR}$ illustrated in FIG. 5) with the frame numbers $F_{n+1}$, $F_{n+3}$, . . . . The first images are captured at different times and are output in chronological order. The same applies to the second images. The images are displayed on the display device 7 in the order of (a), (b), (c), (d), (e), . . . of FIG. 6, for example. As a result, the first images and the second images are alternately displayed on the display device 7. At this time, the camera head 5, the control device 9, and the display device 7 are driven at a frequency that visually leaves an afterimage due to display, for example, at a frequency of 120 Hz or higher. A first display time for displaying the first image and a second display time for displaying the second image may be set differently, or a display pattern may be set such that the same image (for example, the first image) may be continuously displayed in several frames. For example, to continuously display the first image in several frames, a process of displaying the first image in two frames and then displaying the second image in one frame is repeated. At this time, the control unit 97 controls at least one of a timing for image output from the image processing unit 93 to the display device 7 and a timing for image display on the display device 7.

Figure 7:
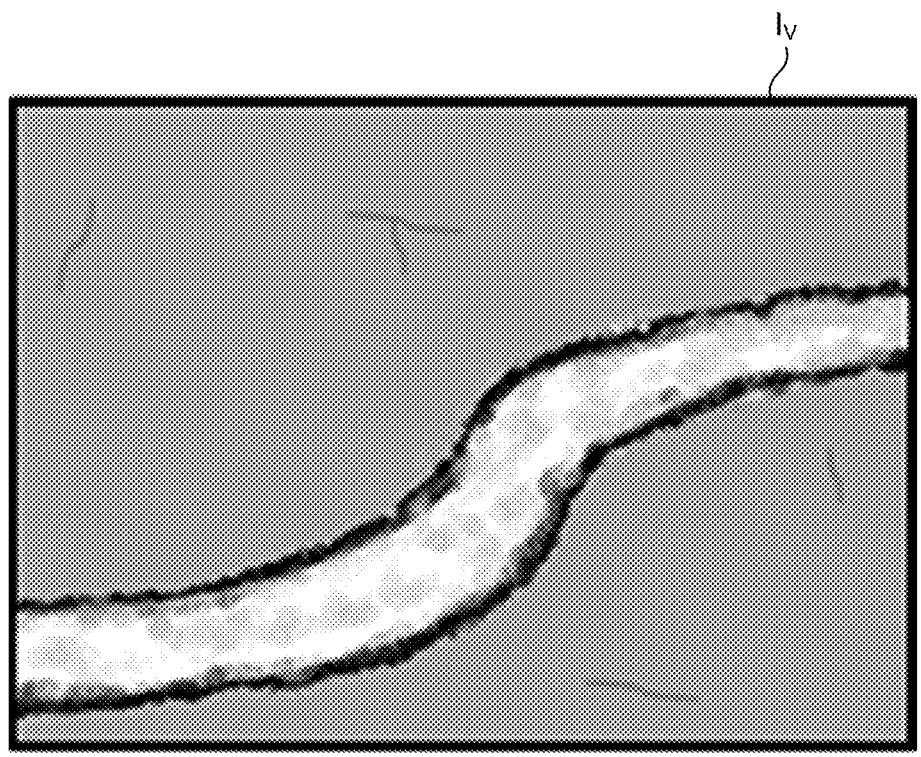
FIG. 7 is a visual image of the first and second images displayed by a display device.

FIG. 7 is a visual image of the first and second images displayed by a display device. When viewing the image in the current frame (for example, the second image $I_{IR}$) with the image in the previous frame (for example, the first image $I_W$) remaining as an afterimage, the observer perceives as if they are looking at a visual image $I_V$ illustrated in FIG. 7. The visual image $I_V$ is an image in which the first image $I_W$ and the second image $I_{IR}$ are combined, which allows the observer to perceive the combined image without actually combining them in the image processing unit 93.

On the other hand, in step S108, the control unit 97 causes the light source device 3 to emit white light. In this case, in the light source device 3, the first light source unit 31 emits white light.

In step S109, among the light emitted from the subject, the first imaging unit 502 receives a component of the white light that has passed through the first filter 501, and performs photoelectric conversion on the light to generate an image signal.

Under the control of the control unit 97, the image processing unit 93 acquires an image signal from the first imaging unit 502 via the communication module 505, the communication module 91, and the data selector 92. For example, the image processing unit 93 acquires a first image $I_W$ as illustrated in FIG. 4.

The image processing unit 93 outputs the first image to the display device 7 (step S110). When not in the special observation mode (when in the normal observation mode), the first image is displayed on the display device. In the normal observation mode, the first image is displayed continuously.

The display conditions may be set such that the brightness of images in the special observation mode is higher than the brightness of images in the normal observation mode. This is because the brightness of the second image is lower than the brightness of the first image in the special observation mode, so it is preferable to brighten the display images which is darker than in the normal observation mode. To handle this, the image processing unit 93 may raise the signal level (brightness value) of images in the special observation mode.

After processing in step S107 or step S110, when an instruction signal for terminating the observation of the subject is input from the input unit 94 (step S111: Yes), the endoscope system 1 terminates this processing. On the other hand, when no instruction signal for terminating the observation of the subject is input from the input unit 94 (step S111: No), the endoscope system 1 returns to step S102 described above.

In the first embodiment described above, the first image based on white light (visible light image) and the second image based on fluorescence of infrared light (fluorescence image) are displayed at different times, which allows the observer to perceive an image in which the first image and the second image were mixed. According to the first embodiment, it is possible to make the visible light image and the fluorescence image perceivable by simple processing.

Second Embodiment

Figure 8:
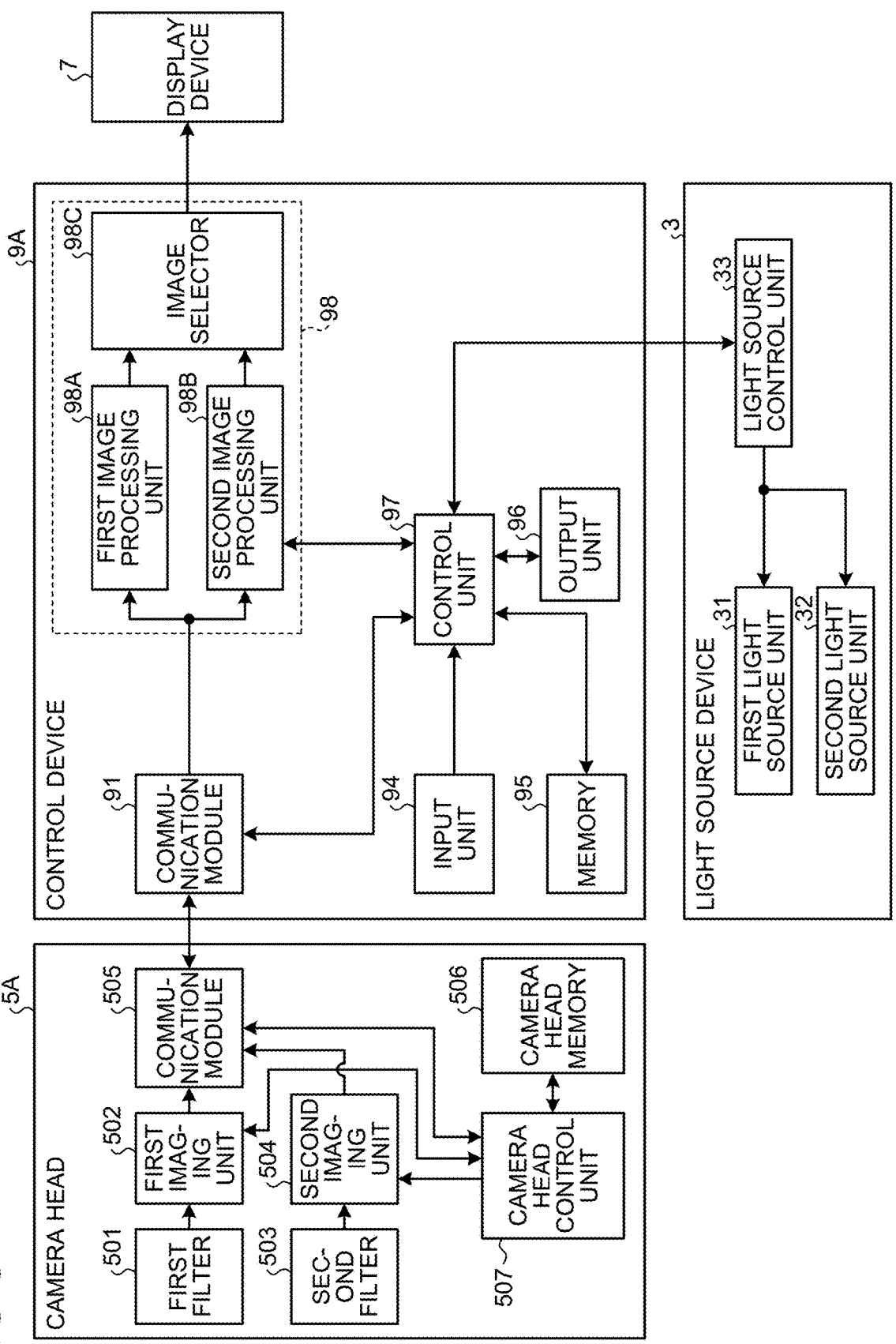
FIG. 8 is a block diagram illustrating a configuration of a camera head, a control device, and a light source device included in an endoscope system according to a second embodiment.

Subsequently, a second embodiment will be described. FIG. 8 is a block diagram illustrating a configuration of a camera head, a control device, and a light source device included in an endoscope system according to the second embodiment. An endoscope system according to the second embodiment includes a control device 9A instead of the control device 9 of the first embodiment described above. In the second embodiment, the components other than the control device 9A are the same as those of the endoscope system 1 of the first embodiment described above, and thus the description thereof will be omitted.

The control device 9A includes the communication module 91, the input unit 94, the memory 95, the output unit 96, the control unit 97, and an image processing unit 98. The image processing unit 98 has a first image processing unit 98A, a second image processing unit 98B, and an image selector 98C. In the second embodiment, the communication module 91 outputs an image signal corresponding to a first image to the first image processing unit 98A under the control of the control unit 97, and outputs an image signal corresponding to a second image to the second image processing unit 98B.

The first image processing unit 98A performs signal processing such as noise reduction processing and A/D conversion processing on the image signal corresponding to the first image received by the communication module 91. Further, the first image processing unit 98A also performs various kinds of image processing on the input image signal under the control of the control unit 97 and outputs the image to the display device 7. The first image processing unit 98A generates a first image and outputs the generated first image to the display device 7. The first image processing unit 98A is configured with a memory and a processor having hardware such as a GPU, FPGA, or CPU.

The second image processing unit 98B performs signal processing such as noise reduction processing and A/D conversion processing on the image signal corresponding to the second image received by the communication module 91. Further, the second image processing unit 98B also performs various kinds of image processing on the input image signal under the control of the control unit 97 and outputs the image to the display device 7. The second image processing unit 98B generates a second image and outputs the generated second image to the display device 7. The second image processing unit 98B is configured with a memory and a processor having hardware such as a GPU, FPGA, or CPU.

Under the control of the control unit 97, the image selector 98C selects images to be displayed on the display device 7 from the images input from the first image processing unit 98A and the second image processing unit 98B, and outputs the images to the display device 7. The image selector 98C outputs the first image (visible light image) and the second image (fluorescence image) to the display device 7 at different times. The image selector 98C is configured with a memory and a processor having hardware such as a GPU, FPGA, or CPU.

In the second embodiment, the endoscope system executes processing according to the above-mentioned flowchart (see FIG. 3). At this time, the first image processing unit 98A executes the image processing related to the first image, and the second image processing unit 98B executes the image processing related to the second image.

In the second embodiment described above, the first image based on white light (visible light image) and the second image based on fluorescence of infrared light (fluorescence image) are displayed at different times, which allows the observer to perceive an image in which the first image and the second image were mixed. According to the second embodiment, it is possible to make the visible light image and the fluorescence image perceivable by simple processing.

Further, in the second embodiment, the image processing of the first image (visible light image) and the image processing of the second image (fluorescence image) are performed in different processing units, which makes the frame rate of display on the display device 7 higher than in the first embodiment.

Third Embodiment

Figure 9:
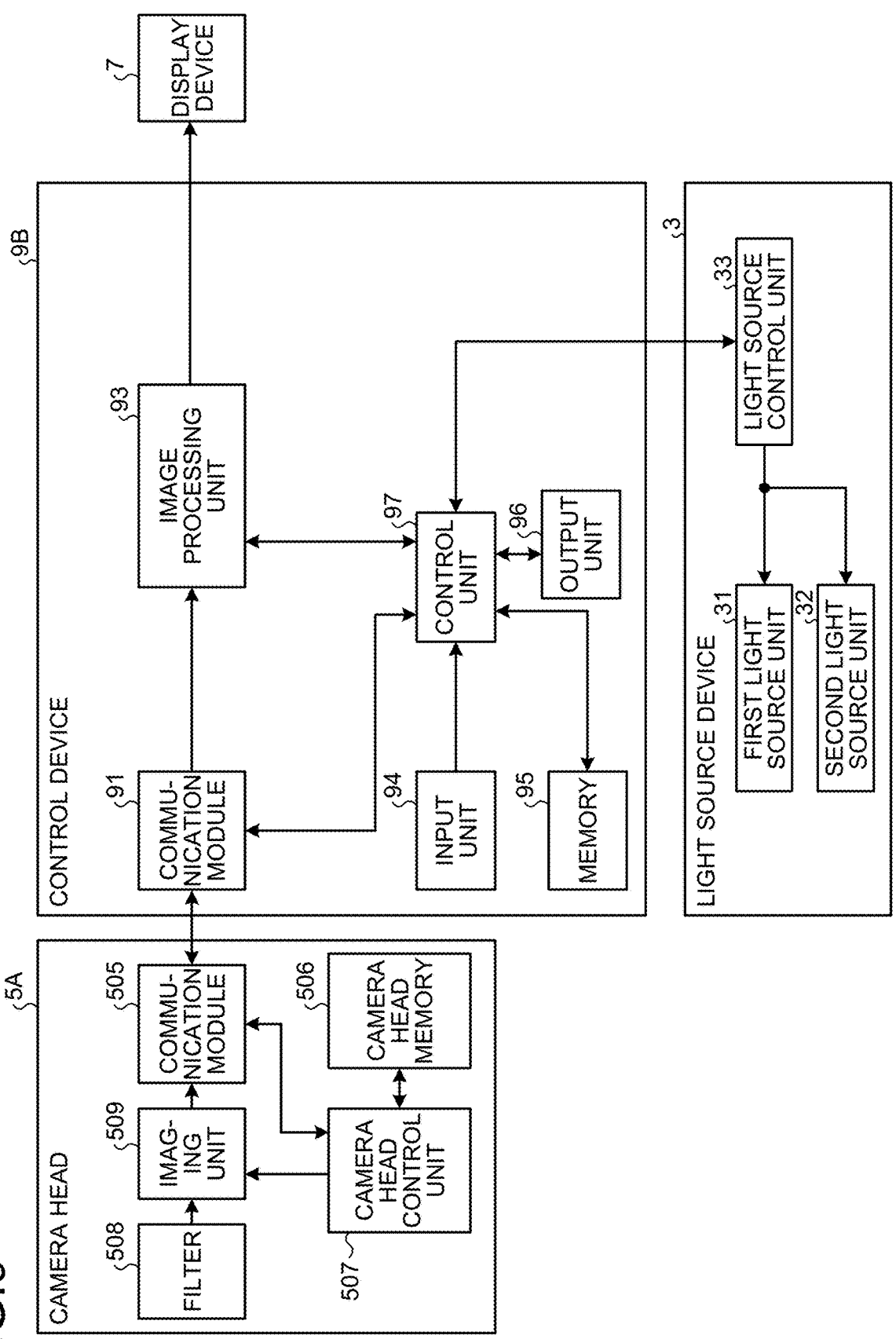
FIG. 9 is a block diagram illustrating a configuration of a camera head, a control device, and a light source device included in an endoscope system according to a third embodiment.

Subsequently, a third embodiment will be described. FIG. 9 is a block diagram illustrating a configuration of a camera head, a control device, and a light source device included in an endoscope system according to the third embodiment. The endoscope system according to the third embodiment includes a camera head 5A and a control device 9B in place of the camera head 5 and the control device 9 of the first embodiment described above. In the third embodiment, the components other than the camera head 5A and the control device 9B are the same as those of the endoscope system 1 of the first embodiment described above, and thus the description thereof will be omitted.

The control device 9B includes the communication module 91, the image processing unit 93, the input unit 94, the memory 95, the output unit 96, and the control unit 97.

The camera head 5A includes the communication module 505, the camera head memory 506, the camera head control unit 507, a filter 508, and an imaging unit 509.

The filter 508 transmits light in a wavelength band emitted by the first light source unit 31 and light in a wavelength band corresponding to fluorescence generated from light emitted by the second light source unit 32, and blocks (reflects) light in wavelength bands other than these wavelength bands.

The imaging unit 509 are configured with an imaging element that receives light (subject image) having passed through the filter 508, performs photoelectric conversion to generate image data (RAW data), and outputs the image data to the communication module 505, under the control of the camera head control unit 507. The imaging unit 509 is configured with a charge coupled device (CCD), a complementary metal oxide semiconductor (CMOS), or the like.

In the third embodiment, under the control of the control unit 97, the light source device 3 alternately controls the first light source unit 31 and the second light source unit 32 to emit white light or infrared light.

In the third embodiment, the endoscope system executes processing according to the above-mentioned flowchart (see FIG. 3). At this time, white light is emitted from the light source device 3 to acquire the first image, and infrared light is emitted from the light source device 3 to acquire the second image.

In the third embodiment described above, the first image based on white light (visible light image) and the second image based on fluorescence of infrared light (fluorescence image) are displayed at different times, which allows the observer to perceive an image in which the first image and the second image were mixed. According to the third embodiment, it is possible to make the visible light image and the fluorescence image perceivable by simple processing.

Further, in the third embodiment, only white light is applied to the subject to acquire the first image (visible light image), and only infrared light is applied to the subject to acquire the second image (fluorescence image). Therefore, as compared with the first embodiment, it is possible to suppress the components of the first image and the components of the second image from being mixed on the image.

Fourth Embodiment

Figure 10:
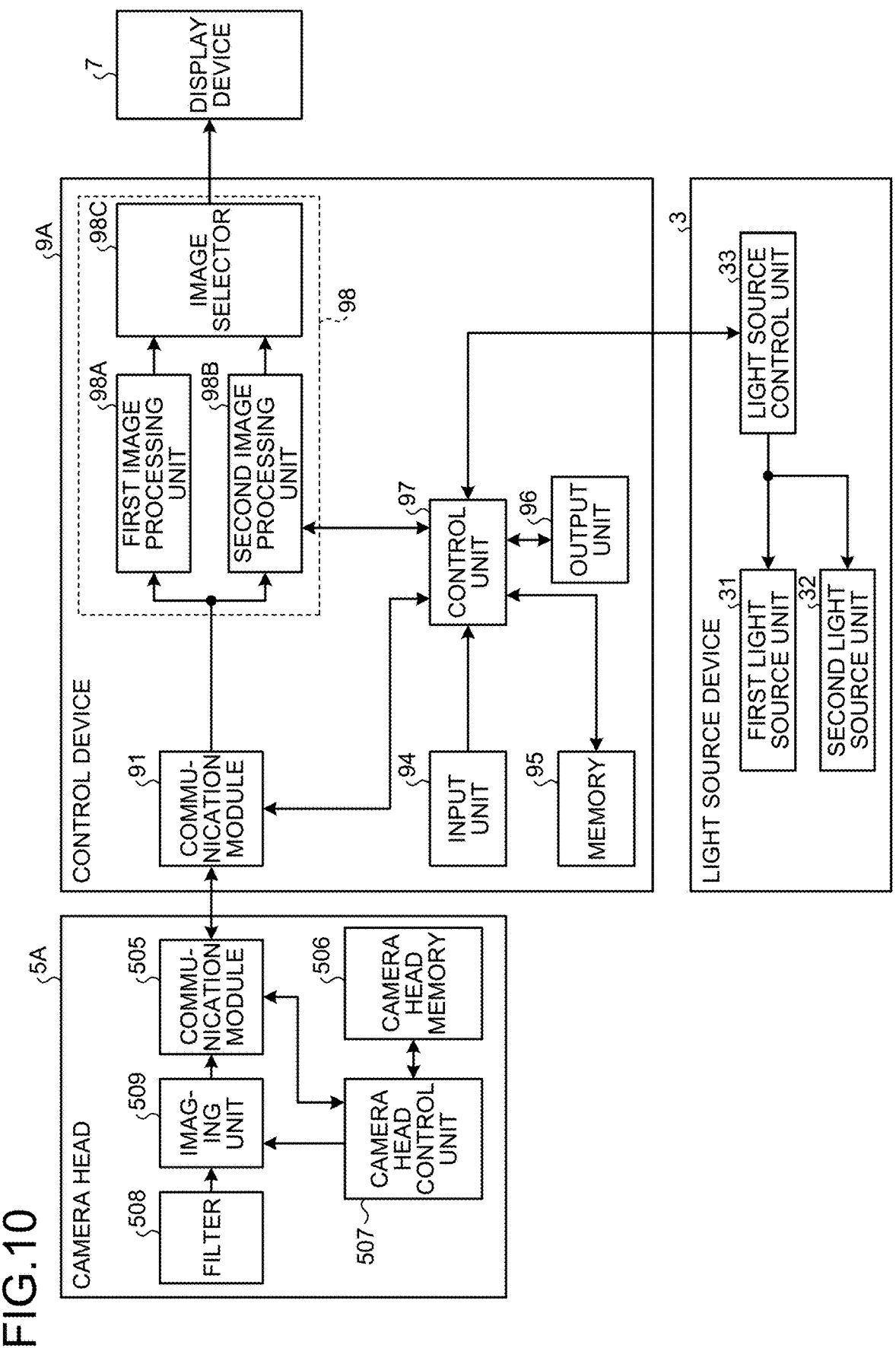
FIG. 10 is a block diagram illustrating a configuration of a camera head, a control device, and a light source device included in an endoscope system according to a fourth embodiment.

Subsequently, a fourth embodiment will be described. FIG. 10 is a block diagram illustrating a configuration of a camera head, a control device, and a light source device included in an endoscope system according to the fourth embodiment. The endoscope system according to the fourth embodiment includes a camera head 5A and a control device 9A in place of the camera head 5 and the control device 9 of the first embodiment described above. In the fourth embodiment, the camera head 5A has the same components as those of the third embodiment, and the control device 9A has the same components as those of the second embodiment.

In the fourth embodiment, the endoscope system executes processing according to the above-mentioned flowchart (see FIG. 3). At this time, white light is emitted from the light source device 3 to acquire the first image, and infrared light is emitted from the light source device 3 to acquire the second image. Further, the first image processing unit 98A executes the image processing related to the first image, and the second image processing unit 98B executes the image processing related to the second image.

In the fourth embodiment described above, the first image based on white light (visible light image) and the second image based on fluorescence of infrared light (fluorescence image) are displayed at different times, which allows the observer to perceive an image in which the first image and the second image were mixed. According to the fourth embodiment, it is possible to make the visible light image and the fluorescence image perceivable by simple processing.

In the fourth embodiment, as in the second embodiment, the image processing of the first image (visible light image) and the image processing of the second image (fluorescence image) are performed in different processing units, which makes the frame rate of display on the display device 7 higher than in the first embodiment.

Further, in the fourth embodiment, as in the third embodiment, only white light is applied to the subject to acquire the first image (visible light image), and only infrared light is applied to the subject to acquire the second image (fluorescence image). Therefore, as compared with the first embodiment, it is possible to suppress the components of the first image and the components of the second image from being mixed on the image.

Fifth Embodiment

Subsequently, a fifth embodiment will be described. In the first embodiment described above, the present disclosure is applied to a rigid endoscope system using a rigid endoscope. However, in the fifth embodiment, the present disclosure is applied to a flexible endoscope system using a flexible endoscope. The same components as those of the endoscope system 1 according to the first embodiment described above are designated by the same reference numerals, and detailed description thereof will be omitted.

Figure 11:
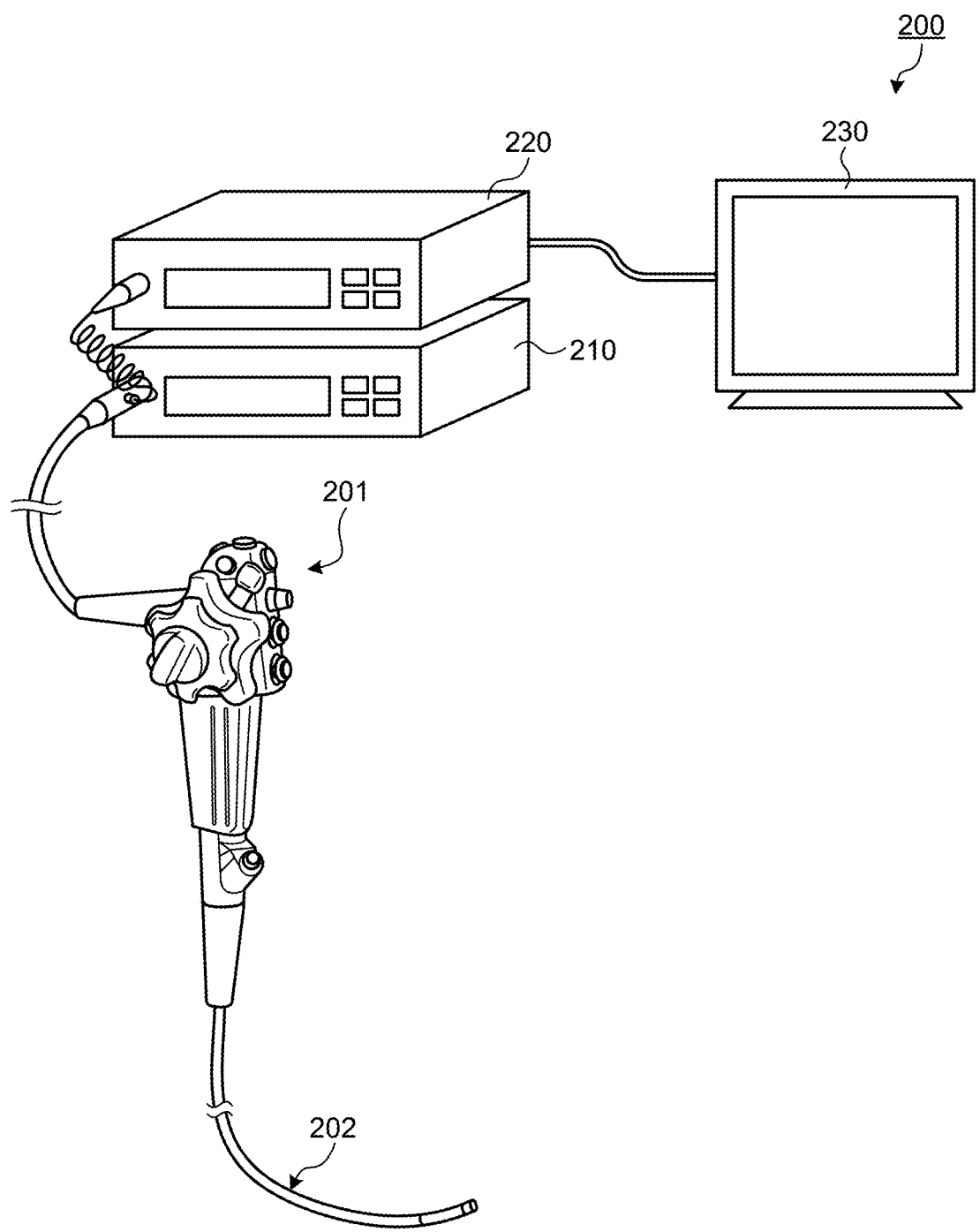
FIG. 11 is a diagram illustrating a schematic configuration of an endoscope system according to a fifth embodiment.

FIG. 11 is a diagram illustrating a schematic configuration of an endoscope system according to the fifth embodiment. An endoscope system 200 illustrated in FIG. 11 includes an endoscope 201 that captures an in-vivo image of an observed region of a subject by inserting an insertion portion 202 into the subject and generates image data, a light source device 210 that supplies white light or infrared light to the endoscope 201, a control device 220 that performs predetermined image processing on an imaging signal acquired by the endoscope 201 and comprehensively controls operations of the entire endoscope system 200, and a display device 230 that displays the in-vivo image on which the control device 220 has performed image processing.

The endoscope 201 has at least the above-mentioned filter and imaging unit.

The light source device 210 has at least the above-mentioned first light source unit 31, second light source unit 32, and light source control unit 33.

The control device 220 includes at least the above-mentioned communication module 91, image processing unit (image processing unit 93, or first image processing unit 98A and second image processing unit 98B), input unit 94, and memory 95, output unit 96, and control unit 97.

According to the fifth embodiment described above, even the flexible endoscope system 200 may obtain the same effects as those of the first embodiment described above.

Sixth Embodiment

Next, a sixth embodiment will be described. In the above-described first to third embodiments, the present disclosure is applied to an endoscope system, but in the sixth embodiment, the present disclosure is applied to a surgical microscope system. The same components as those of the endoscope system 1 according to the first embodiment described above are designated by the same reference numerals, and detailed description thereof will be omitted.

Figure 12:
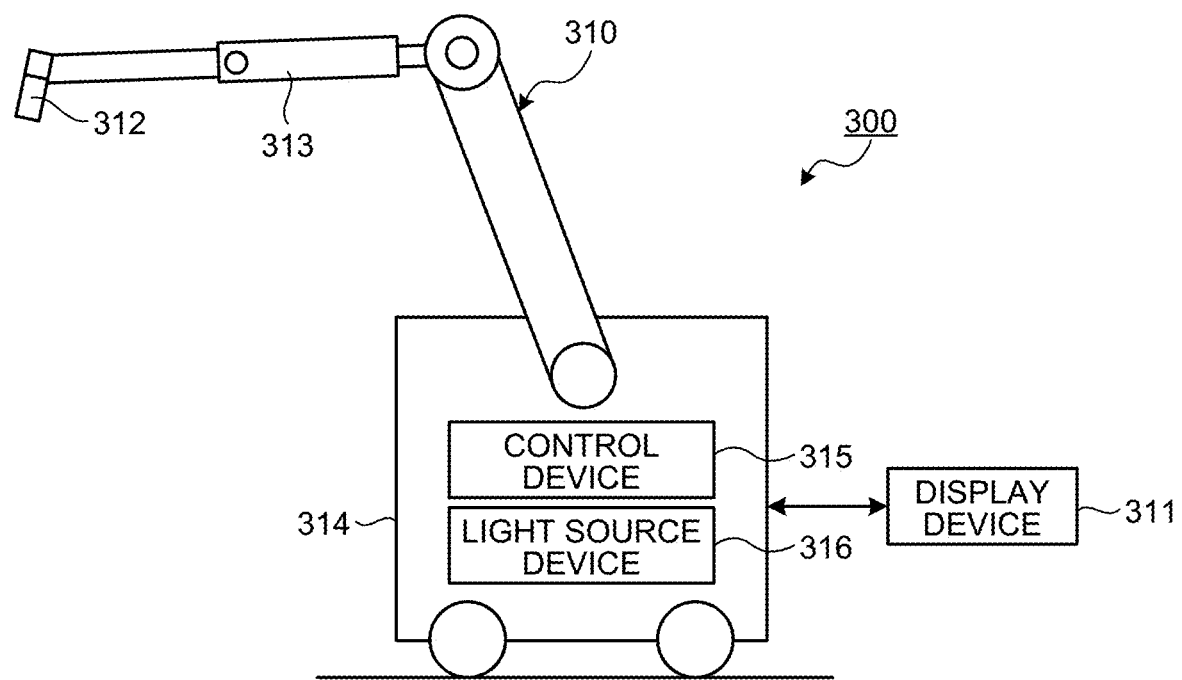
FIG. 12 is a diagram illustrating a schematic configuration of a surgical microscope system according to a sixth embodiment.

FIG. 12 is a diagram illustrating a schematic configuration of the surgical microscope system according to the sixth embodiment. A surgical microscope system 300 illustrated in FIG. 12 includes a microscope device 310, which is a medical imaging device to capture and acquire an image for observing a subject, and a display device 311 that displays the image captured by the microscope device 310. The display device 311 and the microscope device 310 may also be integrally configured.

The microscope device 310 includes a microscope portion 312 that captures an enlarged image of a microscopic portion of a subject, and a support portion 313 that includes an arm connected to a proximal end of the microscope portion 312 to rotatably support the microscope portion 312, and a base portion 314 that rotatably holds the proximal end of the support portion 313 and is movable on the floor surface. The base portion 314 has a control device 315 that controls the operation of the surgical microscope system 300, and a light source device 316 that generates white light, infrared light, or the like with which the subject is to be irradiated from the microscope device 310. The control device 315 includes at least the above-mentioned communication module 91, image processing unit (image processing unit 93, or first image processing unit 98A and second image processing unit 98B), input unit 94, and memory 95, output unit 96, and control unit 97. The light source device 316 also has at least the above-mentioned first light source unit 31, second light source unit 32, and light source control unit 33. The base portion 314 may not be movably provided on the floor surface, but may be fixed to a ceiling, a wall surface or the like to support the support portion 313.

The microscope portion 312 takes, for example, a columnar shape and has the above-mentioned filter and imaging unit therein. A switch that receives an input of an instruction for operating the microscope device 310 is provided on a side surface of the microscope portion 312. A cover glass that protects the inside is provided on the aperture surface at the lower end of the microscope portion 312 (not illustrated).

In the thus configured surgical microscope system 300, a user such as an operator may move the microscope portion 312, perform a zoom operation, or switch illumination light while operating various switches with the microscope portion 312 held by hand. The shape of the microscope portion 312 is preferably elongated and extended in the observation direction so that the user may easily grasp it and change the viewing direction. Therefore, the shape of the microscope portion 312 may be a shape other than a columnar shape, and may be, for example, a polygonal pillar shape.

According to the sixth embodiment described above, the same effects as those of the first embodiment described above may be obtained in the surgical microscope system 300.

OTHER EMBODIMENTS

Variations may be formed by appropriately combining a plurality of components disclosed in relation to the medical observation systems according to the first to sixth embodiments described above. For example, some components may be removed from all the components described in relation to the medical observation systems according to the first to sixth embodiments described above. Further, the components described in relation to the medical observation systems according to the first to sixth embodiments described above may be combined as appropriate.

In the medical observation systems according to the first to sixth embodiments, the above-mentioned "unit" may be read as "means" or "circuit". For example, the control unit may be read as a control means or a control circuit.

Figure 13:
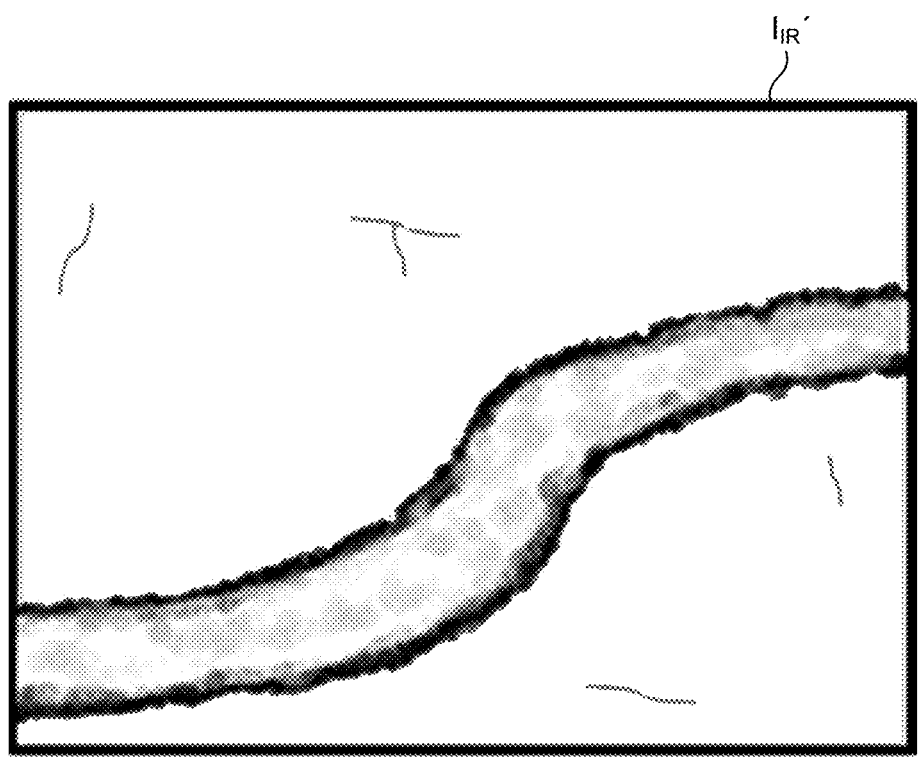
FIG. 13 is a diagram schematically illustrating an example of a second image according to another embodiment.

In the medical observation systems according to the first to sixth embodiments, the image processing unit 93 may extract the fluorescence image (subject) in the second image, and may set an image obtained by replacing the portion other than the fluorescence image with the first image as the second image. The fluorescence image may be extracted by a publicly known method such as contour extraction by edge detection or the like, or by an operator's input instruction. FIG. 13 is a diagram schematically illustrating an example of a second image according to another embodiment. By this replacement, a second image $I_{IR}'$ that is a replacement image in which the region other than the fluorescence image has the same brightness as the first image is generated. By displaying this second image $I_{IR}'$, it is possible to prevent the non-fluorescent portion from being perceived as darker than the corresponding portion in the first image, and to allow this corresponding portion to be perceived with the same brightness as the original first image.

In the medical observation systems according to the first to sixth embodiments, three-dimensional image data may be generated by providing two imaging units for capturing the first image and the second image.

In the medical observation systems according to the first to sixth embodiments, in addition to the first image and the second image, navigation images for guiding the treatment may be alternately displayed.

Programs to be executed by the medical observation systems according to the first to sixth embodiments are provided as file data recorded in an installable format or an executable format in a computer-readable recording medium such as a CD-ROM, a flexible disk (FD), a CD-R, digital versatile disk (DVD), USB medium, or flash memory.

The programs to be executed by the medical observation systems according to the first to sixth embodiments may be stored on a computer connected to a network such as the Internet and provided by downloading via the network.

In the explanation of the timing chart in the present specification, the context of the processing between the timings has been clarified by using expressions such as "first", "then", and "subsequently". However, the order of the processing necessary for carrying out the present disclosure is not uniquely defined by those expressions. That is, the order of the processing in the timing chart described in the present specification may be changed within a consistent scope.

Some of embodiments of the present application have been described in detail with reference to the drawings. However, these are mere examples, and the present disclosure may be carried out in the embodiments disclosed herein and other embodiments in which various modifications and improvements are made based on the knowledge of those skilled in the art.

The present technology may also have the following configurations.

(1) A medical image processing apparatus including
an image processor configured to:
receive a plurality of first image data captured at different times and generated by illumination of light in a first wavelength band in sequence;

receive a plurality of second image data captured at different times and generated by illumination of light in a second wavelength band different from the first wavelength band in sequence;

generate first and second images based on the received first and second image data, respectively; and output the generated first image and second image to a display in chronological order of the first and second images and in accordance with a preset display pattern of the first and second images.

(2) The medical image processing apparatus according to (1), wherein white light and excitation light are emitted at the same time, the first image data is generated based on the white light, and the second image data is generated by the excitation light and fluorescence resulting from the excitation light, and the image processor is configured to generate the first and second images based on the first and second image data, respectively.

(3) The medical image processing apparatus according to (1) or (2), wherein the image processor includes:

a first image processor configured to generate the first image based on the first image data;

a second image processor configured to generate the second image based on the second image data; and an image selector configured to receive the first and second images, select one of the first and second images to be displayed on the display in accordance with the display pattern, and output the selected first or second image.

(4) The medical image processing apparatus according to (2), further including a data selector configured to input the first and second image data input from an external device to the image processor at different times.

(5) The medical image processing apparatus according to (4), wherein the image processor includes:

a first image processor configured to generate the first image based on the first image data, and a second image processor configured to generate the second image based on the second image data.

(6) The medical image processing apparatus according to any one of (1) to (5), wherein the image processor is driven at 120 Hz or higher.

(7) The medical image processing apparatus according to any one of (1) to (6), further including a controller configured to switch between a normal observation mode in which the first image is continuously displayed and a special observation mode in which the first and second images are displayed alternately, wherein a drive frequency in the special observation mode is larger than a drive frequency in the normal observation mode.

(8) The medical image processing apparatus according to any one of (1) to (7), wherein the image processor is configured to alternately output the first image and the second image to the display.

(9) The medical image processing apparatus according to any one of (1) to (8), wherein the image processor is configured to generate a replacement image in which a background region other than a subject in the second image is replaced with a corresponding region of the first image as the second image.

(10) A medical observation system including:

a light source configured to apply white light and excitation light to a subject into which a fluorescent substance has been introduced;

an observation device configured to generate first image data by receiving reflection light from the subject at application of the white light, and generate second image data by receiving light emitted from the fluorescent substance at application of the excitation light;

an image processor configured to generate first and second images based on a plurality of the first image data captured at different times and a plurality of the second image data captured at different times, respectively, which are input from the observation device, and output the generated first image and second image in a chronological order of the images and in accordance with a preset display pattern of the first and second images; and a display configured to display the first and second images output from the image processor.

As described above, the medical image processing apparatus and the medical observation system according to the present disclosure are useful for allowing visible light images and fluorescence images to be perceived by a simple configuration.

According to the present disclosure, it is possible to produce an advantageous effect of making a visible light image and a fluorescence image perceivable by simple processing.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing apparatus comprising an image processor configured to:

receive a plurality of first image data captured at different times and generated by illumination of light in a first wavelength band in sequence;

receive a plurality of second image data captured at different times and generated by illumination of light in a second wavelength band different from the first wavelength band in sequence;

generate first and second images based on the received first and second image data, respectively; and alternately output one of the generated first image and second image at a time to a display in chronological order of the first and second images and in accordance with a preset display pattern of the first and second images, wherein the preset display pattern includes a first display time for the first image that is different from and does not overlap a second display time for the second image.

2. The medical image processing apparatus according to claim 1, wherein white light and excitation light are emitted at the same time, the first image data is generated based on the white light, and the second image data is generated by the excitation light and fluorescence resulting from the excitation light, and the image processor is configured to generate the first and second images based on the first and second image data, respectively.

3. The medical image processing apparatus according to claim 1, wherein the image processor includes:
- a first image processor configured to generate the first image based on the first image data;
- a second image processor configured to generate the second image based on the second image data; and
- an image selector configured to
  - receive the first and second images,
  - select one of the first and second images to be displayed on the display in accordance with the display pattern, and
  - output the selected first or second image.

4. The medical image processing apparatus according to claim 2, further comprising
- a data selector configured to input the first and second image data input from an external device to the image processor at different times.

5. The medical image processing apparatus according to claim 4, wherein the image processor includes:
- a first image processor configured to generate the first image based on the first image data, and
- a second image processor configured to generate the second image based on the second image data.

6. The medical image processing apparatus according to claim 1, wherein the image processor is driven at 120 Hz or higher.

7. The medical image processing apparatus according to claim 1, further comprising
- a controller configured to switch between a normal observation mode in which the first image is continuously displayed and a special observation mode in which the first and second images are displayed alternately, wherein
- a drive frequency in the special observation mode is larger than a drive frequency in the normal observation mode.

8. The medical image processing apparatus according to claim 1, wherein the image processor is configured to alternately output the first image and the second image to the display.

9. The medical image processing apparatus according to claim 1, wherein the image processor is configured to generate a replacement image in which a background region other than a subject in the second image is replaced with a corresponding region of the first image as the second image.

10. A medical observation system comprising:
- a light source configured to apply white light and excitation light to a subject into which a fluorescent substance has been introduced;
- an observation device configured to
  - generate first image data by receiving reflection light from the subject at application of the white light, and
  - generate second image data by receiving light emitted from the fluorescent substance at application of the excitation light;
- an image processor configured to
  - generate first and second images based on a plurality of the first image data captured at different times and a plurality of the second image data captured at different times, respectively, which are input from the observation device, and
  - output one of the generated first image and second image at a time in a chronological order of the images and in accordance with a preset display pattern of the first and second images, wherein the preset display pattern includes a first display time for the first image that is different from and does not overlap a second display time for the second image; and
- a display configured to display the first and second images output from the image processor.

11. The medical observation system according to claim 10, wherein the image processor includes
- a first image processor configured to generate the first image based on the first image data; and
- a second image processor configured to generate the second image based on the second image data.

12. The medical observation system according to claim 11, further comprising
- an image selector configured to
  - receive the first and second images,
  - select one of the first and second images to be displayed on the display in accordance with the display pattern, and
  - output the selected first or second image.

13. The medical observation system according to claim 10, wherein the first display time includes a different number of frames than the second display time.

14. The medical image processing apparatus according to claim 1, wherein the first display time includes a different number of frames than the second display time.

* * * * *